United States Patent [19]

Gately et al.

[11] Patent Number: 5,650,492

[45] Date of Patent: Jul. 22, 1997

[54] P-40 HOMODIMER OF INTERLEUKIN-12

[75] Inventors: Maurice Kent Gately, Pine Brook, N.J.; John Hakimi, Scarsdale, N.Y.; Ping Ling, Nutley, N.J.

[73] Assignee: Hoffmann-La Roche Inc., Nutley, N.J.

[21] Appl. No.: 424,682

[22] Filed: Apr. 18, 1995

Related U.S. Application Data

[63] Continuation of Ser. No. 87,832, Jul. 2, 1993, abandoned.

[51] Int. Cl.$^6$ .......................... C07K 14/54; A61K 38/20
[52] U.S. Cl. .......................... 530/351; 530/402; 530/408; 930/141; 424/85.2
[58] Field of Search .......................... 530/351, 402, 530/408; 930/141; 424/85.2

[56] References Cited

FOREIGN PATENT DOCUMENTS

| | | |
|---|---|---|
| 325 224 | 7/1989 | European Pat. Off. . |
| 418 014 | 3/1991 | European Pat. Off. . |
| 476 983 | 3/1992 | European Pat. Off. . |
| 92/05256 | 4/1992 | WIPO . |

OTHER PUBLICATIONS

Brod, S., et al., *J. Immunol.*, 147:810 (1991).
Campbell, I.L., et al., *J. Clin. Invest.*, 87:739 (1991).
Chan, S.H., et al., *J. Exp. Med.*, 173:869 (1991).
Chizzonite, R., et al., *J. Immunol.*, 148:3117 (1992).
Chizzonite, R., et al., *J. Immunol.*, 147:1548 (1992).
D'Andrea, A., et al., *J. Exp. Med.*, 176:1387 (1992).
Desai, B.B., et al., *J. Immunol.*, 148:3125 (1992).
Desai, B.B., et al., *J. Immunol.*, 150:207A (1993).
Doherty, G.M., et al., *J. Immunol.*, 149:1666 (1992).
Gately, M.K., et al., *J. Immunol.*, 147:874 (1991).
Gately, M.K., et al., *Cell. Immunol.*, 143:127 (1992).
Gearing, D.P., et al., *Cell*, 66:9 (1991).
Gubler, U., et al., *Proc. Natl. Acad. USA*, 88:4143 (1991).
Guesdon, J-N., et al., *J. Histochem. Cytochem.*, 27:1131 (1979).
Hibi, M., et al., *Cell*, 63:1149 (1990).
Hori, T., et al., *Blood*, 70:1069 (1987).
Hseih, C-S, et al. *Science*, 260:547–549 (1993).
Hunkapiller, M.W., et al., "Methods of Protein Microcharacterization" (Shively, J.E., Ed), The Humana Press, Clifton, NJ, p. 315 (1986).
Jacob, C.O., et al., *J. Exp. Med.*, 166:798 (1987).
Kishimoto, T., et al., *Science*, 258:593 (1992).
Kobayashi, M., et al., *J. Exp. Med.*, 170:827 (1989).
Laemmli, U.K., *Nature*, 227:680 (1970).
Manetti, R., et al., *J. Exp. Med.*, 177:1199 (1993).
Mattner, F., et al., *Eur. J. Immunol.*, 23:2202–2208 (1993).
Merzberg, D.M., *Immunology Today*, 13:77 (1992).
Mizushima, S., et al., *Nucleic Acids Research*, 18:5322 (1990).
Podlaski, F.J., et al., *Arch. Biochem Biophy.*, 294:230 (1992).
Sambrook, J. et al., "Molecular Cloning: A laboratory manual. 2nd Edition, Cold Spring Harbor Press", NY (1989) (not enclosed).
Schlaak, J., et al., *Eur. J. Immunol.*, 22:2771 (1992).
Schoenhaut, D.S., et al., *J. Immunol.*, 148:3433 (1992).
Stern, A.S., et al., *Proc. Natl. Acad. Sci. USA*, 87:6808 (1990).
Summers, M.D., et al., "A manual of methods for baculovirus vectors and insect cell culture procedures". TX A&M Univ. 1987) (not enc.).
Taga, T., et al., *Cell*, 58:573 (1989).
Wolf, S., et al., *FASEB J.*, 6:A1335 (1992).
Wolf, S.F., et al., *J. Immunol.*, 146:3074 (1991).
Massague, J., *Annu. Rev. Cell Biol.*, vol. 6:597–641 (1990).
Oefner, C., et al., *The EMBO Journal*, vol. 11(11), pp. 3921–3926 (1992).
Ling, P. et al., Journal of Immunology, 154(1):117–127 (1995).

*Primary Examiner*—John Ulm
*Assistant Examiner*—Prema Mertz
*Attorney, Agent, or Firm*—George W. Johnston; Dennis P. Tramaloni; Alan P. Kass

[57] ABSTRACT

Analysis of the culture media of p40-transfected COS cells indicated the presence of 40 kDa monomers and 80 kDa disulfide-linked homodimers. Examination of partially purified p40 recombinant proteins demonstrated that only the homodimer but not the monomer binds to the IL-12 receptor. Partially purified 80 kDa homodimer inhibited [$^{125}$I]IL-12 binding to PHA-activated human lymphoblasts with an IC$_{50}$ of 80 ng/ml, which is similar to the IC$_{50}$ value (20 ng/ml) for the human IL-12 heterodimer. Although neither the 40 kDa monomer nor the 80 kDa dimer could stimulate human PHA-blast proliferation, the 80 kDa dimer inhibited IL-12-induced proliferation in a dose-dependent manner with an IC$_{50}$ of 1 µg/ml. The IL-12 p40 subunit contains the essential epitopes for receptor binding, but they are only active when p40 is covalently associated with a second protein such as p35 or p40. When p40 is associated with the p35 subunit, the heterodimer acts as an agonist mediating biologic activity. When p40 associates with itself, the homodimer behaves as an antagonist.

8 Claims, 12 Drawing Sheets

P-40 HOMODIMER OF INTERLEUKIN-12

This is a continuation of application Ser. No. 08/087,832, filed Jul. 2, 1993 now abandoned.

FIELD OF THE INVENTION

This invention relates to a protein of two p40 subunits of interleukin-12 linked by at least one disulfide bond which acts as an interleukin-12 receptor antagonist.

BACKGROUND OF THE INVENTION

Interleukin-12 (IL-12), formerly known as cytotoxic lymphocyte maturation factor (CLMF) or natural killer cell stimulatory factor (NKSF), is a cytokine that has pleiotropic activities including stimulation of the proliferation of activated T and NK cells (1, 2), induction of INF-γ production by peripheral blood mononuclear cells (2, 3), and enhancement of the lytic activity of NK/LAK cells (2, 4).

IL-12 is a heterodimeric molecule with an approximate molecular weight of about 75 kDa consisting of two disulfide-linked subunits: p35, having an approximate molecular weight of about 35 kDa, and p40, having an approximate molecular weight of about 40 kDa, (2, 4–6). The p40 subunit shares amino acid sequence homology with the interleukin-6 receptor (IL-6R) (7) and therefore belongs to the cytokine receptor superfamily, whereas p35 has a distant but significant relationship to the IL-6/G-CSF cytokine family (8). It has been speculated that the p35/p40 heterodimer could represent a cytokine (p35) and soluble cytokine receptor (p40) complex, with the cellular IL-12 receptor providing function analogous to the IL-6 signal transducing protein, gp130 (7, 8).

The biological activity of IL-12 is mediated by the binding of the intact IL-12 molecule to plasma membrane receptors on activated T or NK cells (9,10); however, the contributions of the individual subunits to receptor binding and signal transduction remain unknown. Studies with neutralizing antibodies to human IL-12 (11) and site-specific chemical modification (12) suggested that the p40 subunit contains epitopes important for IL-12 binding to its receptor. Also, studies with human/mouse chimeric molecules indicated that p35 is responsible for the species specificity of the heterodimer for biological activities (13).

We investigated both the binding and biological activities of each IL-12 subunit. COS cells transfected with only the p40 cDNA produced both p40 monomer and p40 homodimer having an approximate molecular weight of about 80 kDa, the latter capable of binding to the IL-12 receptor but unable to mediate cellular proliferation. The 80 kDa p40 homodimer acts as a receptor antagonist useful in regulating the biological activity of IL-12 in immune responses.

SUMMARY OF THE INVENTION

The present invention is directed towards an isolated and purified protein comprising two p40 subunits of interleukin-12 which are associated together, preferably by at least one disulfide bond, having a molecular weight of about 80 kDa. The 80 kDa p40 homodimer acts as an interleukin-12 receptor antagonist. The preferred p40 subunit is that of SEQ. ID NO:1.

BRIEF DESCRIPTION OF THE DRAWINGS

FIG. 1A: curve a represents nonspecific staining of cells incubated only with biotinylated-8E3 and streptavidin-PE. Curves b and c represent cells incubated with 100 and 500 ng/ml of human IL-12, respectively. FIG. 1B: curve a represents nonspecific staining, and curves b, c, d, and e represent cells incubated with 2.5, 12.5, 125 and 500 ng/ml of rp40, respectively.

DETAILED DESCRIPTION OF THE INVENTION

Figure 1A:
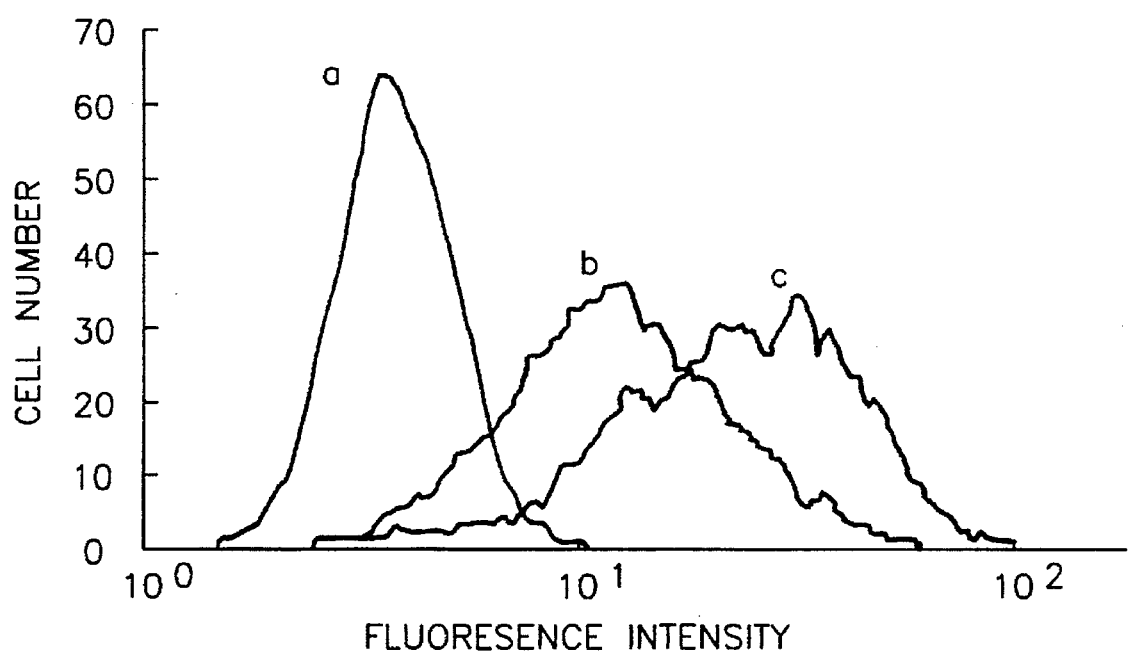
FIG. 1A and 1B. Dose-response binding of human IL-12 and COS-expressed rp40 to KIT225/K6 cells analyzed by flow cytometry. Varying concentrations of purified human IL-12 or rp40 containing conditioned medium (determined by EIA (enzyme immunoassay) using IL-12 as standard) were incubated with KIT225/K6 cells and detected with biotinylated 8E3 mAb followed by streptavidin-PE as described in the Materials and Methods.

The present invention is directed towards an isolated and purified protein comprising two p40 subunits of interleukin 12 associated together, preferably by at least one disulfide bond, having a molecular weight of about 80 kDa. The 80 kDa p40 homodimer acts as an interleukin-12 receptor antagonist. The preferred p40 subunit is that of SEQ ID NO:1.

The IL-12 p40 homodimer is useful as an IL-12 antagonist to block the biological activity of IL-12 in pathologic immune responses. Current evidence from both in vitro and in vivo studies suggest that IL-12 plays an important role in the development of Th1-type helper T cells which promote cell-mediated immune responses (22,27), in triggering gamma interferon production by mature T and/or NK cells (28), and in facilitating specific cytolytic T lymphocyte responses (29). Excessive activity of Th1 cells (30, 31) and/or excessive production of gamma interferon (32–34) may be involved in the pathogenesis of some autoimmune disorders and septic shock, indicating that IL-12 p40 homodimer should be useful in the treatment of disorders such as rheumatoid and other inflammatory arthritides, Type I diabetes mellitus, multiple sclerosis, systemic lupus erythematosus, septic shock, etc. In addition, IL-12 p40 homodimer should be useful in preventing or delaying homograft rejection and graft versus host disease. In using IL-12 p40 homodimer to prevent or reverse pathologic immune responses, it can be combined with other cytokine antagonists such as antibodies to the IL-2 receptor, soluble TNF receptor, or the IL-1 receptor antagonist, and the like.

The dose ranges for the administration of the p40 homodimer protein may be determined by those of ordinary skill in the art without undue experimentation. In general, appropriate dosages are those which are large enough to produce the desired effect, for example, blocking the binding of IL-12 to its receptor. The dosage should not be so large as to cause adverse side effects, such as unwanted cross-reactions, anaphylactic reactions, and the like. Generally, the dosage will vary with the age, condition, sex and extent of disease in the patient, counter indications, if any, immune tolerance and other such variables, to be adjusted by the individual physician. The p40 homodimer protein can be administered parenterally by injection or by gradual perfusion over time. It can be administered intravenously, intraperitoneally, intramuscularly, or subcutaneously.

Pharmaceutically acceptable carriers and preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, inert gases and the like. See, generally, *Remington's Pharmaceutical Science.* 16th Ed., Mack Eds., 1980.

The invention also relates to method for preparing a medicament or pharmaceutical composition comprising the P40 homodimer protein of the invention.

MATERIALS AND METHODS

Cell lines.

KIT225/K6, an IL-2-dependent subclone derived from the human T cell line KIT225 (14), was obtained from Dr. T. Waldmann, NIH/NCI (Bethesda, Md.). These cells were previously found to express IL-12 receptors (15). KIT225/K6 cells were cultured in RPMI 1640 medium (BioWhittaker, Walkersville, Md.) supplemented with 2 mM L-glutamine (Sigma, St. Louis, Mo.), 100 U/ml penicillin, 100 µg/ml streptomycin (Gibco, Grand Island, N.Y.), 15% FCS (JRH Biosciences, Lenexa, Kans.), and 100 U/ml human rIL-2 (Dr. F. Khan, Hoffmann-La Roche, Nutley, N.J.). COS cells were cultured in DMEM (Gibco) with 4500 mg/liter glucose, 2 mM L-glutamine, 50 U/ml penicillin, 50 µg/ml streptomycin and 10% FCS (JRH Biosciences).

Expression of IL-12 subunits.

The IL-12 expression constructs for COS-expression were built in the pEF-BOS vector which contains the promoter of the human polypeptide chain elongation factor 1α(EF-1α) chromosomal gene (16a). The cDNA fragments containing the entire coding region of the human or mouse p40 or p35 cDNAs generated by polymerase chain reaction (PCR) using the primers complementary to the beginning and end of the subunit cDNA coding sequences as described previously (6, 13) were subcloned individually into the pEF-BOS vector at the Xba 1 cloning site by blunt end ligation (standard procedure). The ligation products were transformed into *E. coli* strain DH-5 alpha, and the resulting colonies were screened by PCR for the correct insert orientation by using a forward primer within the pEF-BOS promoter and a reverse primer within the subunit coding sequences. Positive clones were selected and amplified in *E. coli* strain MC 1161. Plasmid DNAs were prepared by using the QIAGEN plasmid kit (Ojagen, Chatsworth, Calif.) and transfected into COS cells by using the DEAE dextran/chloroquine method (17). The DNAs at a concentration of 2 μg/ml were mixed with 10% Nutridoma-SP (Boehringer Mannheim, Indianapolis, Ind.), 0.5 mg/ml DEAE dextran and 0.05 mg/ml chloroquine in DMEM (Dulbelcco's modified essential medium) medium and applied to COS cells seeded for 16 h. After a 2.5–3 h incubation, the cells were treated with 10% DMSO in serum free DMEM medium for 3 min followed by washing with DMEM medium, and then cultured in DMEM/10% FCS medium. Supernatant fluids were collected from the cultures of transfected COS cells after 72 h. Coexpression of p40 and p35 subunits was performed by mixing the two plasmid DNAs at a 1:1 (W/W) ratio in transfection reagents. The supernatant fluids derived from the COS cultures transfected with pEF-BOS wild-type plasmid DNA were used as controls.

The human IL-12 p40 construct for expression in Baculovirus system was built in pACDZ-1 vector (16b) (obtained from R. Gentz, F. Hoffmann-La Roche Ltd, Basel, Switzerland) at BamH1 site by using same approach described above. A recombinant baculovirus expressing the p40 chain was generated by cotransfecting SF9 cells with wild type baculovirus DNA and the p40 expressing plasmid pACDZ-1. Limited dilution cloning in microtiterplates was used to isolate a single recombinant baculovirus expressing the human IL-12 p40 subunit.

IL-12 receptor binding and proliferation assays.

The binding of COS-expressed IL-12 molecules to IL-12 receptor-bearing cells was measured by FACS (fluorecense activated cell sorthing) analysis essentially as described by Desai et al.(10). Briefly, $1\times10^6$ KIT225/K6 cells suspended in 25 μl of FACS buffer (PBS (phosphate-buffered-saline) /2% FCS/0.05% sodium azide) were incubated with IL-12 preparations (25μl) at room temperature for 40 min, followed by incubation with biotinylated mAb 8E3 (5 μg/ml, 50 μl), (11) for 30 min, and then with streptavidin-PE (1.5 μg/ml, 50 μl; FisherBiotech, Pittsburgh, Pa.) for 20 min. The stained cells were analyzed on a FACScan flow cytometer (Becton Dickinson). Specificity of binding was determined by preincubating the IL-12 preparations (0.5 μg/ml) with 4A1 (25 μg/ml), a rat inhibitory anti-human IL-12 monoclonal antibody, prior to adding cells. Control samples were incubated with normal rat IgG (25 μg/ml). The receptor binding properties of the COS-expressed IL-12 molecules were also evaluated in an [$^{125}$I]IL-12 competitive receptor binding assay performed essentially as previously described (11). 0.1 ml aliquots of serial dilutions of culture supernatant fluids or purified IL-12 were mixed with 0.05 ml aliquots of binding buffer (RPMI-1640, 5% FCS, 25 mM HEPES pH 7.4) containing [$^{125}$I]IL-12 ($2\times10^6$ cpm). The mixture was added to 0.1 ml of activated blasts ($1\times10^7$ cell/ml) and incubated in a shaking water bath at 25° C. for 1.5 h. Non-specific binding was determined by inclusion of 20 μg/ml unlabeled IL-12 in the assay. Incubations were carried out in duplicate. Cell bound radioactivity was separated from free [125I]IL-12 by centrifugation of 0.1 ml aliquots of the assay contents in duplicate through 0.1 ml silicone oil for 90 sec at 10.000× g. The tip containing the cell pellet was excised and cell bound radioactivity was determined in a gamma counter.

The biological activity of COS-expressed IL-12 molecules was evaluated in proliferation assays using 4-day PHA-activated human lymphoblasts previously described (4, 13).

Anti-IL-12 antibodies and sandwich enzymatic immunoassay (EIA).

Goat and rabbit anti-human IL-12 antisera were obtained from animals immunized with purified human rIL-12 that had been expressed in CHO cells (kindly provided by Dr. A. Stern, Hoffmann-La Roche Inc., Nutley, N.J.). The IgG fraction was isolated from 100 ml of the antisera by Protein-G Sepharose (Pharmacia LKB, Piscataway, N.J.) affinity chromtography according to the manufacturer's procedures. Anti-human IL-12 antibodies were purified from the IgG fractions on a human IL-12-conjugated hydrazide AvidGel F. (BioProbe International) immunoaffinity column (1.5×2.0 cm, 0.55 mg protein per ml resin). Biotinylation of the antibodies using Biotin X-NHS (Calbiochem, San Diego, Calif.) was performed as described previously (18). Monoclonal antibodies 4A1 and 8E3 are rat antibodies specific for the p40 subunit of human IL-12 (11) (kindly provided by Dr. Richard Chizzonite, Hoffmann-La Roche Inc., Nutley, N.J.).

The IL-12 sandwich EIA, using mAb 4A1 as a capture antibody and peroxidase-conjugated 8E3 as detection antibody, was performed as described previously (11). This assay detects IL-12 heterodimer and p40 subunit but not p35 subunit. Therefore, a second IL-12 sandwich EIA using polyclonal antibodies was developed to detect both p40 and p35. In this assay, 96 well EIA plates (Nunc MaxiSorp, Thousand Oaks, Calif.) were coated with affinity-purified goat anti-human IL-12 antibody (2 μg/ml, 50 μl/well) at 4° C. overnight and blocked with 1% BSA in PBS pH 7.4 for 1 h at RT. Serial dilutions of IL-12 and culture supernatant fluids were applied to the plates, and incubated at RT for 2.5 h. The plates were subsequently incubated with biotinylated, affinity-purified rabbit anti-human IL-12 antibody (500 ng/ml, 50 μl/well), followed by peroxidase-conjugated streptavidin (1 μg/ml, 50 μl/well, Sigma, St. Louis, Mo.). Color was developed with 100 μl of 1 mM ABTS (2.2'-azinobis(3-ethylbenzthiazolinesulfonic acid)/0.1% (v/v) $H_2O_2$, and the absorbance at 405 nm was determined with a Vmax Kinetic. Microplate reader (Molecular Devices, Palo Alto, Calif.). All values are based on an IL-12 standard curve with no corrections calculated for differences in molecular weights of monomers or dimers.

Immunoprecipitation.

Immunoprecipitation of COS-expressed IL-12 subunits and heterodimers was performed as described (17). Briefly, 0.5 ml supernatant fluids from transfected COS cultures were incubated with 5 μg IgG protein isolated from goat anti-IL-12 antiserum at 4° C. on a rotating mixer overnight. The immune complexes were adsorbed onto Protein G-Sepharose (50% suspension, 10 μl, Pharmacia LKB) at 4° C. for 2 h, and the beads were washed twice with 1 ml NET-Gel buffer (50 mM Tris-HCl, pH 7.5, 150 mM NaCl, 0.1% (v/v) Nonidet P-40, 1 mM EDTA, 0.25% (w/v) gelatin and 0.02% (w/v) sodium azide), and once with 1 ml of 10 mM Tris-HCl (pH 7.5) containing 0.1% (v/v) Nonidet P-40. The bound proteins were dissociated from the beads by heating for 3 min at 95° C. in either reducing (10% 2-ME) or non-reducing SDS sample buffer.

SDS-PAGE and Western blotting.

SDS-PAGE was performed according to the method of Laemmli (19). Western blotting was performed by electrophoretically transferring proteins to a nitrocellulose membrane (0.2μ) (MSI, Westboro, Mass.). The transferred membranes were blocked by incubation in PBST buffer (PBS with 0.05% v/v Tween-20) containing 5% (w/v) non-fat dry milk, and then probed with anti-IL-12 rabbit antisera (1:500 dilution). After three washes with PBST buffer, the membranes were incubated at room temperature with peroxidase-conjugated donkey anti-rabbit IgG antibodies (1:1000 dilution) (Jackson Immuno Research, West Grove, Pa.). The color was developed by use of 4-chloro-1-napthol (BioRad, Richmond, Calif.) in 20 mM Tris-HCl buffer (pH 7.5) containing 0.1% (v/v) $H_2O_2$.

Purification of COS-expressed P40.

One liter of conditioned media containing approximately 3 μg/ml of human recombinant p40 (rp40) was applied to a mAb 4A1-conjugated NuGel (NITS) immunoaffinity column (2.5×10 cm, containing 1.6 mg antibody per ml gel, kindly provided by Dr. A. Stern, Hoffmann-La Roche Inc., Nutley, N.J.) at a flow rate of 2 ml/min, and the column was washed extensively with PBS containing 0.5M NaCl and 0.2% Tween 20 until absorbance monitoring at 280 mn was less than 0.01. The bound proteins were then eluted with 100 mM glycine/150 mM NaCl (pH 2.8) at a flow rate of 2 ml/min, and 20 ml fractions were collected and immediately neutralized with 1/10 vol. of 1M Tris-HCl (pH 8.0). The EIA-positive fractions were pooled, dialyzed against PBS overnight at 4° C., concentrated by ultrafiltration using YM 10 membranes (Amicon, Beverly, Mass.) to 5 ml, and applied onto a HiLoad Superdex 75 (Pharmacia LKB) column (1.6×60 cm) equilibrated with Dulbecco's PBS buffer. The column was eluted at a flow rate of 1 ml/min with the same buffer, and 1 ml fractions were collected. Proteins from each fraction were examined by EIA, SDS-PAGE and Western blot analysis.

Deglycosylation.

500 ng of pure human IL-12 or immunoprecipitated rp40 protein was denatured by heating at 95° C. for 5 rain in 0.25M $Na_2HPO_4$ (pH 7.2), 0.5% SDS with or without 1% 2-ME. The samples were cooled to room temperature, adjusted to 1% Nonidet P-40, 20 mM EDTA, and then treated with 0.1 U of N-glycosidase F (Boehringer Mannheim, Indianapolis, Ind.) at 37° C. for 24 h. The deglycosylated proteins were examined by SDS-PAGE and Western blot analysis.

Amino-terminal sequence analysis of COS-expressed p40.

The immunoaffinity purified rp40 proteins were separated on 10% non-reducing SDS gel and transferred electrophoretically to an Immobilon™ PVDF membrane (Millipore, Bedford, Mass.). The bands at ~80 and ~40 kDa identified by Coomassie blue staining were subjected to automated Edman degradation on an Applied Biosystems Model 470A gas-phase sequencer with on-line analysis of phenylthiohydantoin (PTH) amino add derivatives as described previously (20).

RESULTS

Expression and characterization of human IL-12 subunits.

Human IL-12 subunits p35 and p40, or human IL-12 p35/p40 heterodimer were expressed by transfecting either subunit cDNA independently or cotransfecting both cDNAs at a 1:1 (w:w) ratio in COS cells. Secretion of the recombinant proteins was evaluated by two different EIA's. The p40-specific monoclonal antibody-based EIA was capable of detecting the p40 subunit and the p40/p35 heterodimer. The IL-12 specific polyclonal EIA was also capable of detecting the p35 subunit. Using human IL-12 as a standard, the concentration range of rp40 and rp35/rp40 proteins in the conditioned media was 0.5–3.0 μg/ml, whereas the expression of rp35 alone was approximately 0.2 μg/ml. It remains unclear whether the p35 expression was low or the sensitivity of the polyclonal EIA in detecting p35 was poor.

Figure 1B:
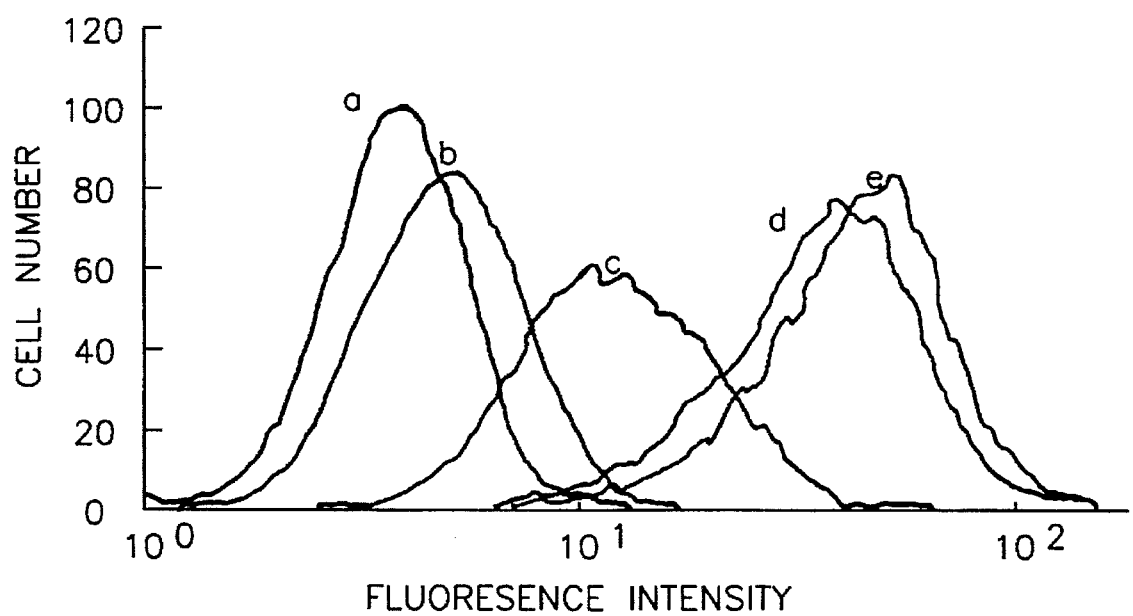
Figure 2A:
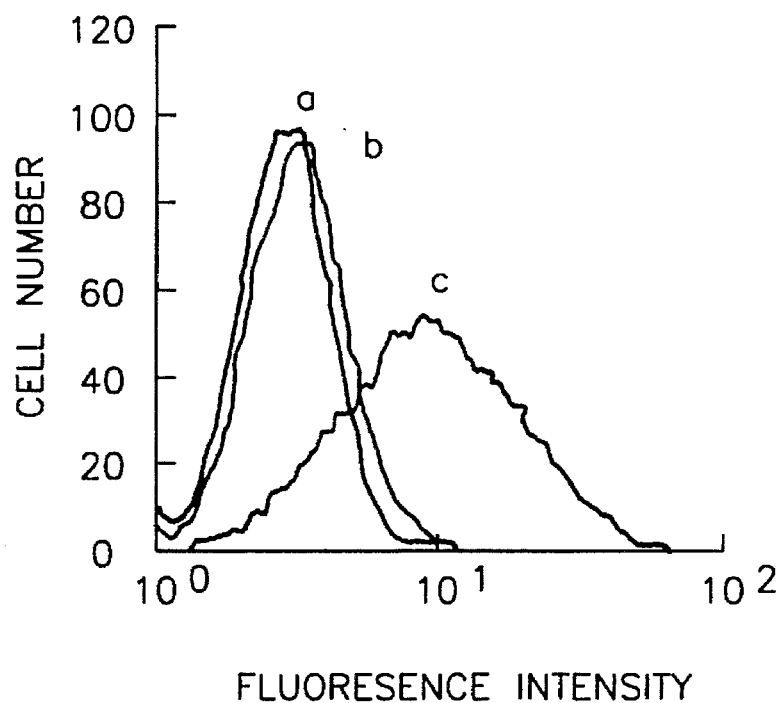
FIGS. 2A, 2B, 2C and 2D. Specificity of rp40 binding to KIT225/K6 cells detected by FACS analysis. Purified human IL-12 (FIG. 2A), conditioned media from cultures of COS cells cotransfected with human p35 and p40 cDNAs (FIG. 2B), or with human p40 cDNA alone (FIG. 2C) were diluted to 0.5 μg/ml (determined by EIA) and incubated with 4A1 neutralizing monoclonal anti-human IL-12 antibody (b) or with normal rat IgG (R-IgG) (c) at a final concentration of 25 g/ml at room temperature for 1 h prior to addition of KIT225/K6 cells. Conditioned medium from culture of COS cells transfected with pEF-BOS wild type plasmid was used as a control (FIG. 2D). To measure nonspecific staining, cells were incubated with only biotin-8E3 and streptavidin-PE (a).
Figure 2B:
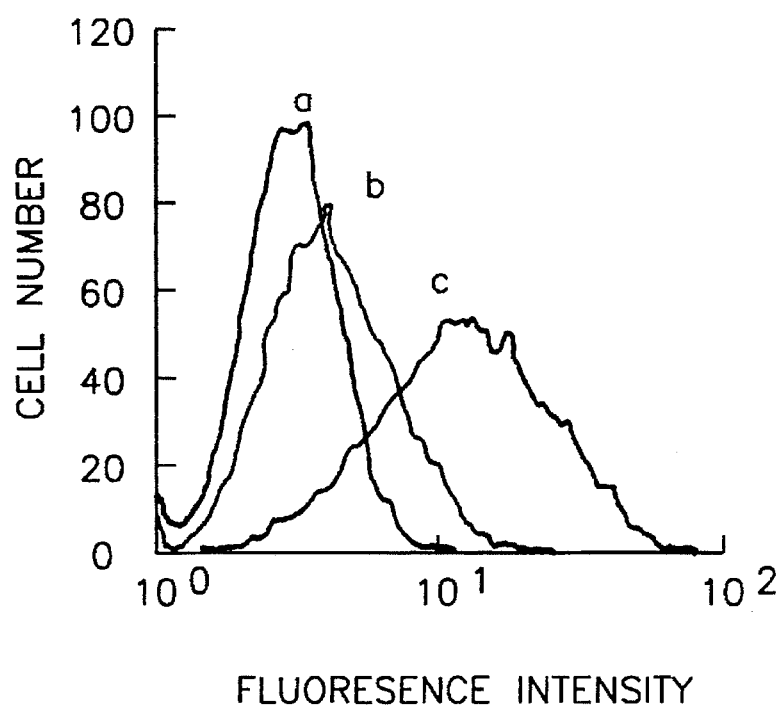
Figure 2C:
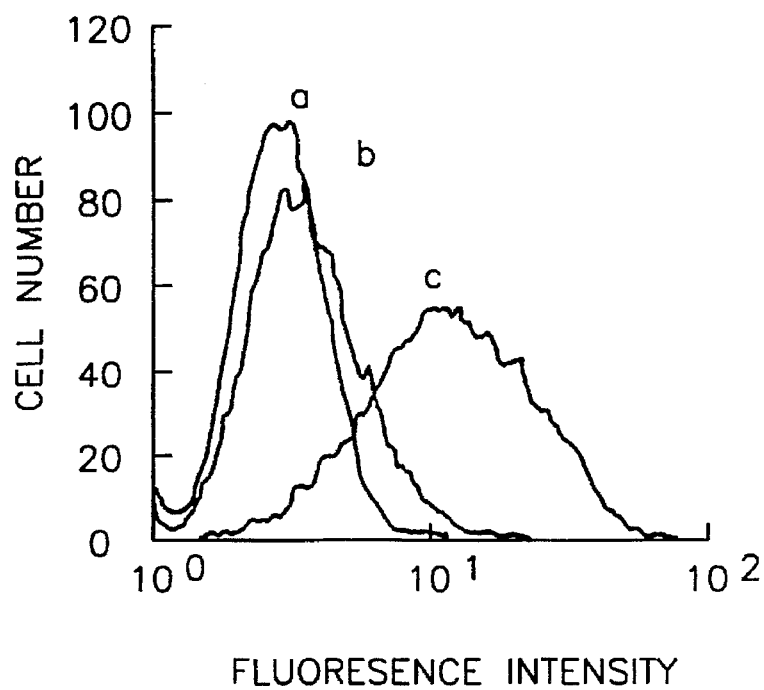
Figure 2D:
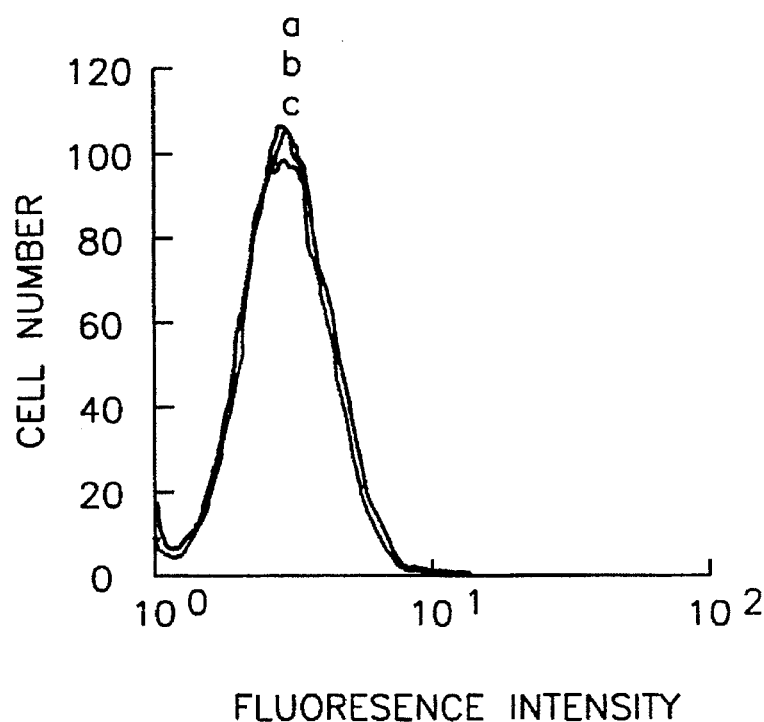

The COS-expressed human IL-12 recombinant proteins were initially examined for their ability to inhibit the binding of [$^{125}$I]human IL-12 to PHA-activated human lymphoblasts. The rp40 supernatants at a 1:2 dilution exhibited 30–40% inhibition of [$^{125}$I]IL-12 binding in three independent experiments, whereas the rp35 supernatants were inactive. The binding of rp40 to the IL-12 receptor was further characterized by flow cytometry using KIT225/K6 cells which constitutively express IL-12 receptors (IL-12R) (15). Dose-dependent binding of human IL-12 and rp40 to KIT225/K6 was observed in the range of 2.5–500 ng/ml (FIGS. 1A and 1B). Specificity of the binding was demonstrated by achieving greater than 80% inhibition of the binding by preincubation of IL-12 or rp40 with an inhibitory rat anti-human p40 monoclonal antibody, 4A1 (FIGS. 2A, 2B, 2C and 2D). Normal rat IgG had no effect on IL-12 or rp40 binding.

Figure 3:
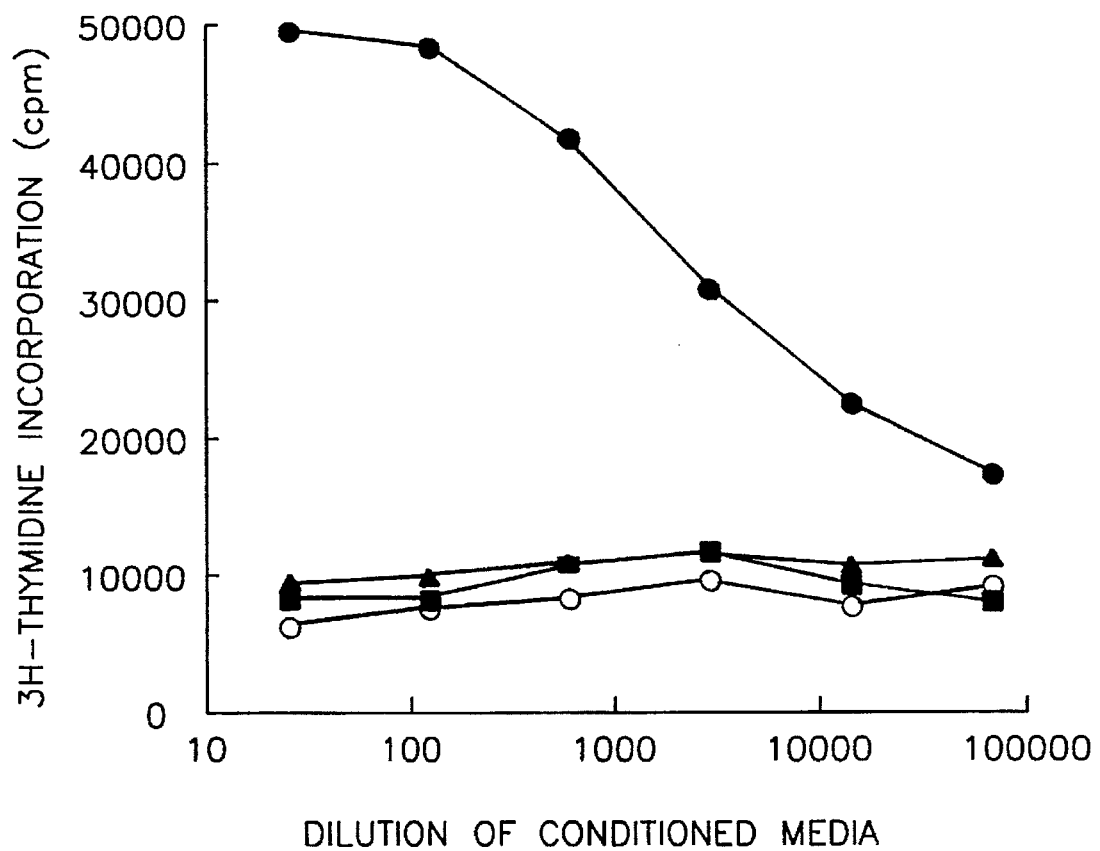
FIG. 3. Proliferation of PHA-activated-human lymphoblasts in response to conditioned media containing individually expressed rp40 and rp35, or coexpressed rp35/rp40. Human PHA(phytohemagglutinin)-blasts were cultured with serial dilutions of the conditioned media from cultures of COS cells transfected with human p35 and p40 cDNA (-●-), p40 cDNA alone (-■-), p35 cDNA alone (-♦-), or pEF-BOS wild type plasmid (-○-). [$^3$H]thymidine incorporation was measured after 48 h as described in Materials and Methods.

Conditioned media containing the COS-expressed IL-12 subunit proteins were evaluated in the human PHA-blast proliferation assay (FIG. 3). The rp35/rp40-containing medium supported T cell proliferation in a dose-dependent manner with an apparent $EC_{50}$ of 8 ng/ml. The rp40 supernatants did not induce proliferation at concentrations equivalent to the rp35/rp40 supernatant.

Characterization of the rp40 40 kDa and 80 kDa species.

Figure 4A:
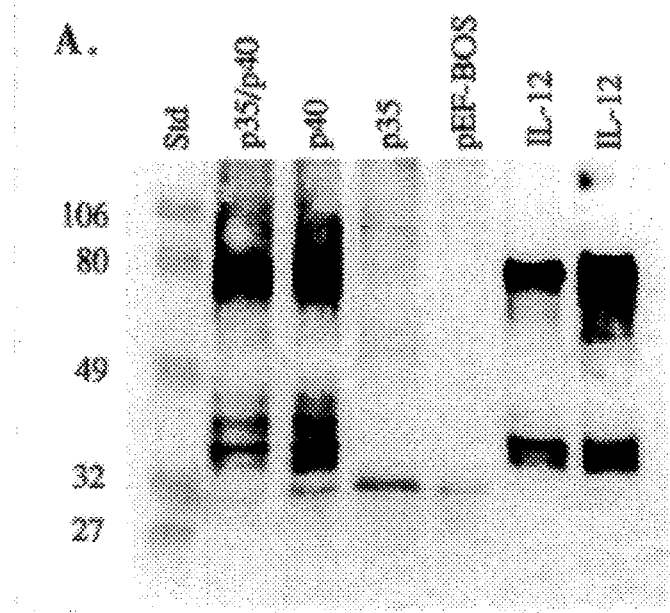
FIGS. 4A and 4B. Western blot analysis of COS-expressed human rp35, rp40 and rp35/rp40 heterodimer proteins. Conditioned media (0.5 ml) were immunoprecipitated with 5 μg IgG protein isolated from goat anti-human IL-12 antisera, separated by SDS/PAGE under nonreducing (FIG. 4A) or reducing (FIG. 4B) conditions and analyzed by immunoblot using rabbit anti-human IL-12 antisera and peroxidase-conjugated donkey anti-rabbit IgG. Samples loaded to each lane were as indicated. Human IL-12 from CHO cells was loaded with two different doses (50 ng and 200 ng, respectively) for comparison. Positions of molecular weight standards (×10$^{-3}$) are shown on the left.
Figure 4B:
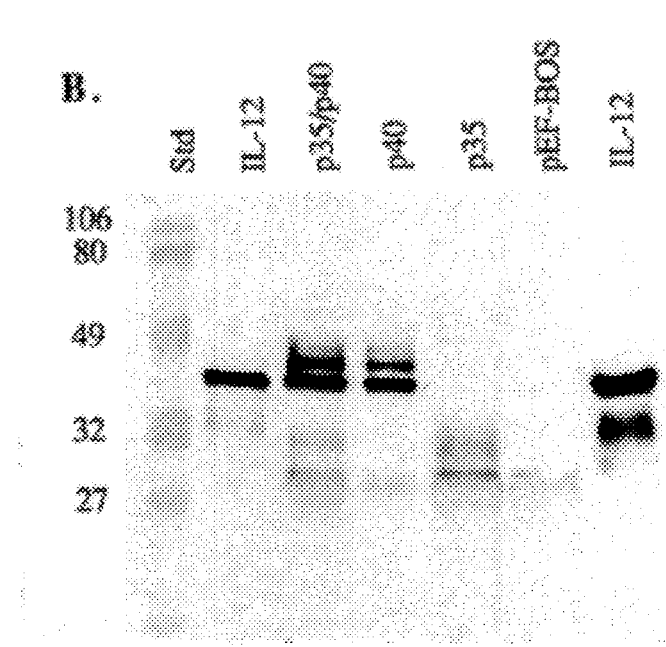
Figure 5A:
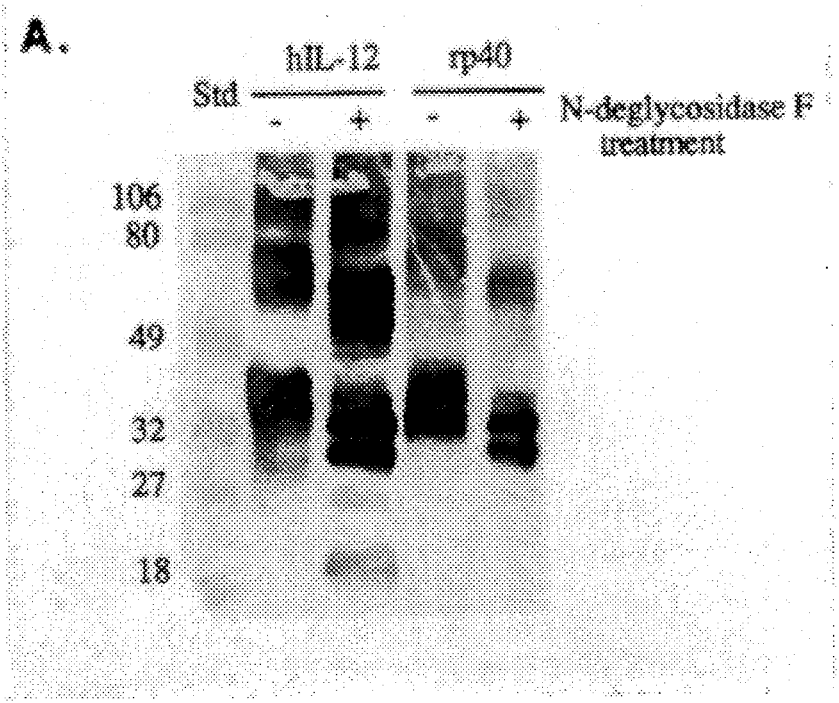
FIGS. 5A and 5B. Deglycosylation of COS-expressed human rp40 proteins. Purified human IL-12 (0.5 μg) and COS-expressed human rp40 proteins immunoprecipitated with goat anti-human IL-12 antisera were deglycosylated by N-deglycosidase F as described in Materials and Methods. Duplicate samples of the deglycosylated proteins were separated by SDS/PAGE under nonreducing (FIG. 5A) or reducing (FIG. 5B) conditions and analyzed by immunoblot as described in Materials and Methods. Positions of molecular weight standards (×10$^{-3}$) are shown on the left.

The recombinant human IL-12 subunits were immunoprecipitated with anti-human IL-12 goat antiserum and characterized by SDS-PAGE and Western blot analysis. Analysis of the rp40 expressed by COS cells transfected with only the p40 cDNA revealed two sets of multiple bands under nonreducing conditions with heterogeneous molecular weights of 70–85 kDa and 35–45 kDa (FIG. 4A). Under reducing conditions, only three closely spaced bands at approximately 38–49 kDa were identified suggesting that the 80 kDa proteins are disulfide-linked rp40 homodimers (FIG. 4B). Treatment of the rp40 immunoprecipitates with N-deglycosidase-F shifted both molecular weight species down to smaller products under nonreducing conditions (FIG. 5A), and converted the reduced triple bands to a single 36 kDa product similar to p40 subunit of the deglycosylated human IL-12 (12) demonstrating that the multiple bands of rp40 expressed in COS cells are due to glycosylation heterogeneity.

In contrast, the immunoprecipitation of rp35 protein revealed only a single band with a molecular weight of 35 kDa under reducing conditions (FIG. 4B). Under nonreducing conditions, a set of lightly stained bands were found at 60–70 kDa suggesting that rp35 may also partially form dimers. However, the polyclonal goat anti-IL-12 antibody poorly recognized the rp35proteins (FIG. 4A). Coexpression of p35 and p40 gave a pattern of bands which was a mixture of those seen when each subunit was expressed independently (FIGS. 4A and 4B). It is unclear whether the p35/p40 heterodimer and the p40/p40 homodimer were produced simultaneously by COS cells cotransfected with the p35 and p40 cDNAs. Unfortunately, currently available reagents do not distinguish the p35/p40 heterodimer from the p40/p40 homodimer.

To confirm the identity of the two rp40 species, the rp40 proteins were partially purified by 4A1 immunoaffinity chromatography. Only 60% of EIA positive material was recovered by elution with 100 mM glycine containing 150 mM NaCl at pH 2.8. The 4A1 affinity-purified proteins were then separated by SDS-PAGE, electrophoretically transferred to a PVDF membrane, and subjected to amino acid microsequencing. One broad band at ~80 kDa and two bands at 35–40 kDa gave $NH_2$-terminal sequences identical to that of native human IL-12 p40 purified from NC-37 cells (4, 12) (Table I). No trace of p35 sequences as identified with the rp40 species. This result confirmed that the 80 kDa protein is a p40 homodimer.

TABLE I

Amino-terminal Sequences of COS-expresssed Human p40 Monomer, p80 Homodimer and Native Human IL-12 p40 subunit

| Protein | Sequence |
| --- | --- |
| Native Human p40 | I W E L K K D V Y V$^a$ [SEQ ID NO: 2] |
| rp40 Dimer | I W$^b$ E L k k D V Y V [SEQ ID NO: 2] |
| rp40 Monomer (band 1) | I w E L k k D V Y V [SEQ ID NO: 2] |
| rp40 Monomer (band 2) | I W E L k k D V Y V [SEQ ID NO: 2] |

$^a$From Podlaski et al., 1991
$^b$Small case letter represents a signal with a recovery less than 2 pmol.

Figure 6A:
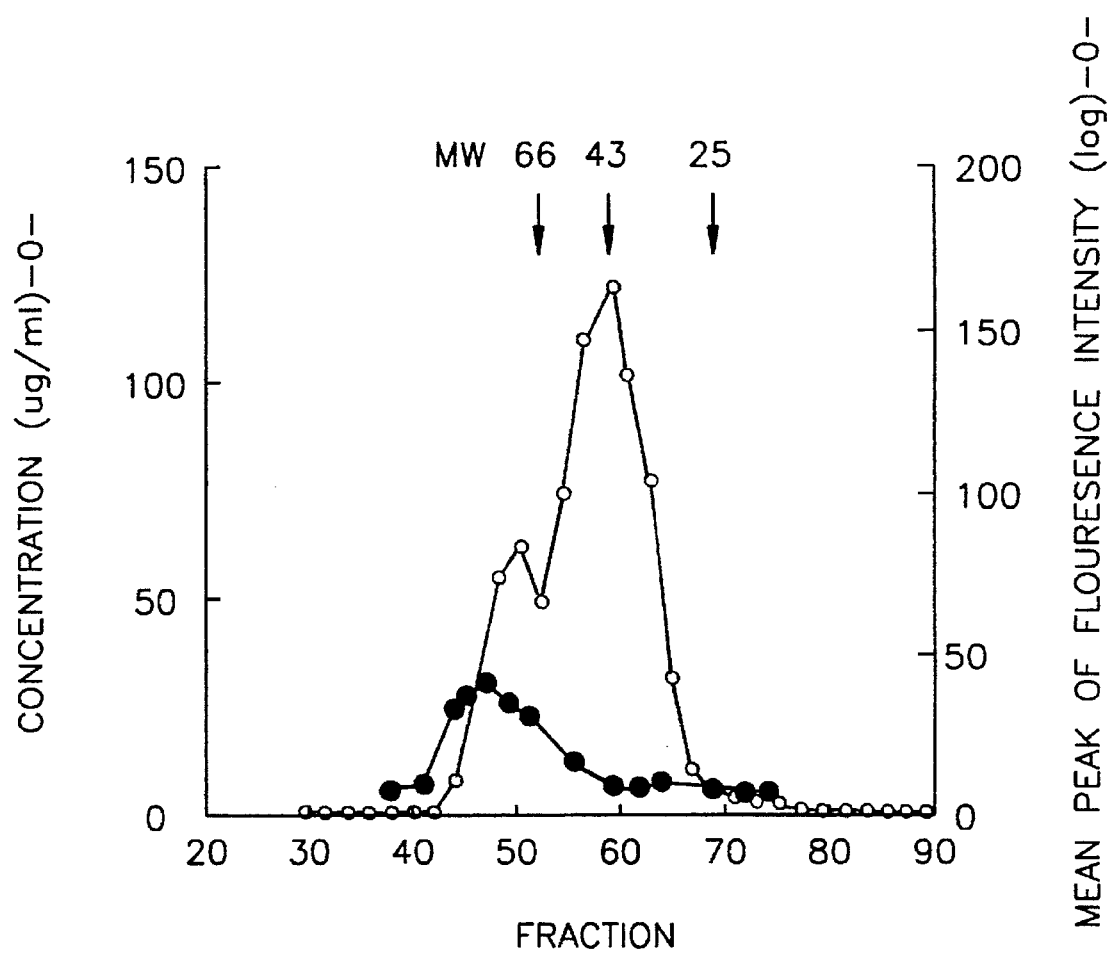
FIGS. 6A and 6B. HPLC fractionation of rp40 species. Recombinant p40 proteins were partially purified by immunoaffinity chromatography and applied onto a HiLoad Superdex 75 gel filtration column. The fractions were evaluated in the p40 EIA and the KIT225/K6 FACS binding assay. The EIA data (-○-) were plotted as μg/ml (using human IL-12 as a standard), and the binding data (-●-) were plotted as the mean peak of fluorescence intensity (FIG. 6A). The EIA positive fractions were evaluated by nonreducing SDS-PAGE and Western blot analysis (FIG. 6B). Lanes 1 to 12 represent the proteins (~50 ng) from fractions 40, 44, 46, 48, 50, 52, 54, 58, 60, 62, 64, and 70, respectively.
Figure 6B:
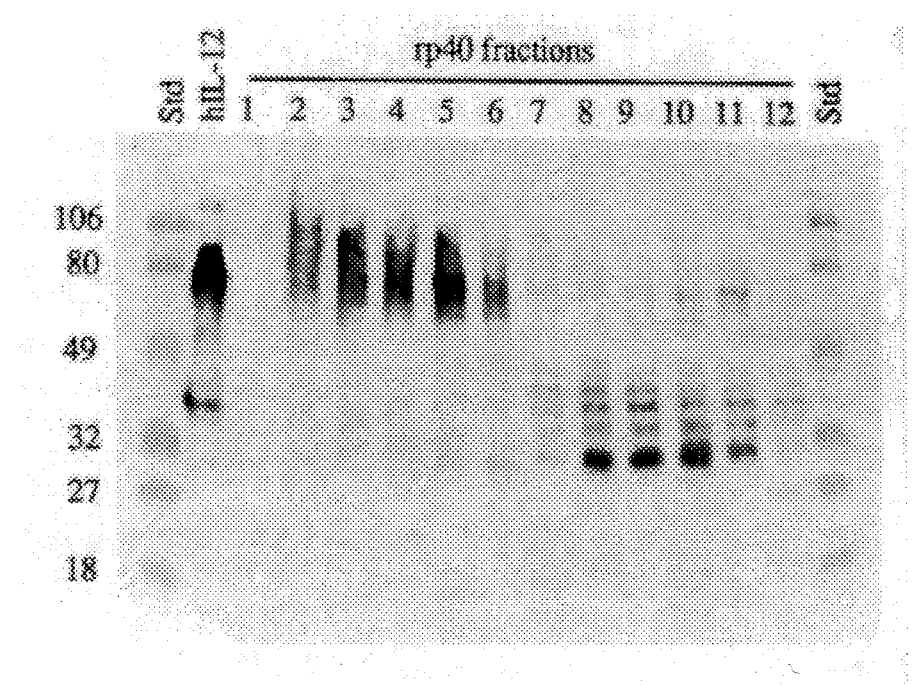

The immunoaffinity purified p40 proteins were further fractionated by Superalex-75 gel filtration chromatography. Two EIA positive protein peaks were identified at molecular weights corresponding to 80 kDa and 40 kDa (FIG. 6A). SDS-PAGE and Western blot analysis of the fractions confirmed the separation of dimer from monomer rp40 (FIG. 6B). The ratio of the monomer to dimer varied from experiment to experiment, but, on the average, approximately 30% of the COS-expressed rp40 was p40 homodimer.

Figure 7:
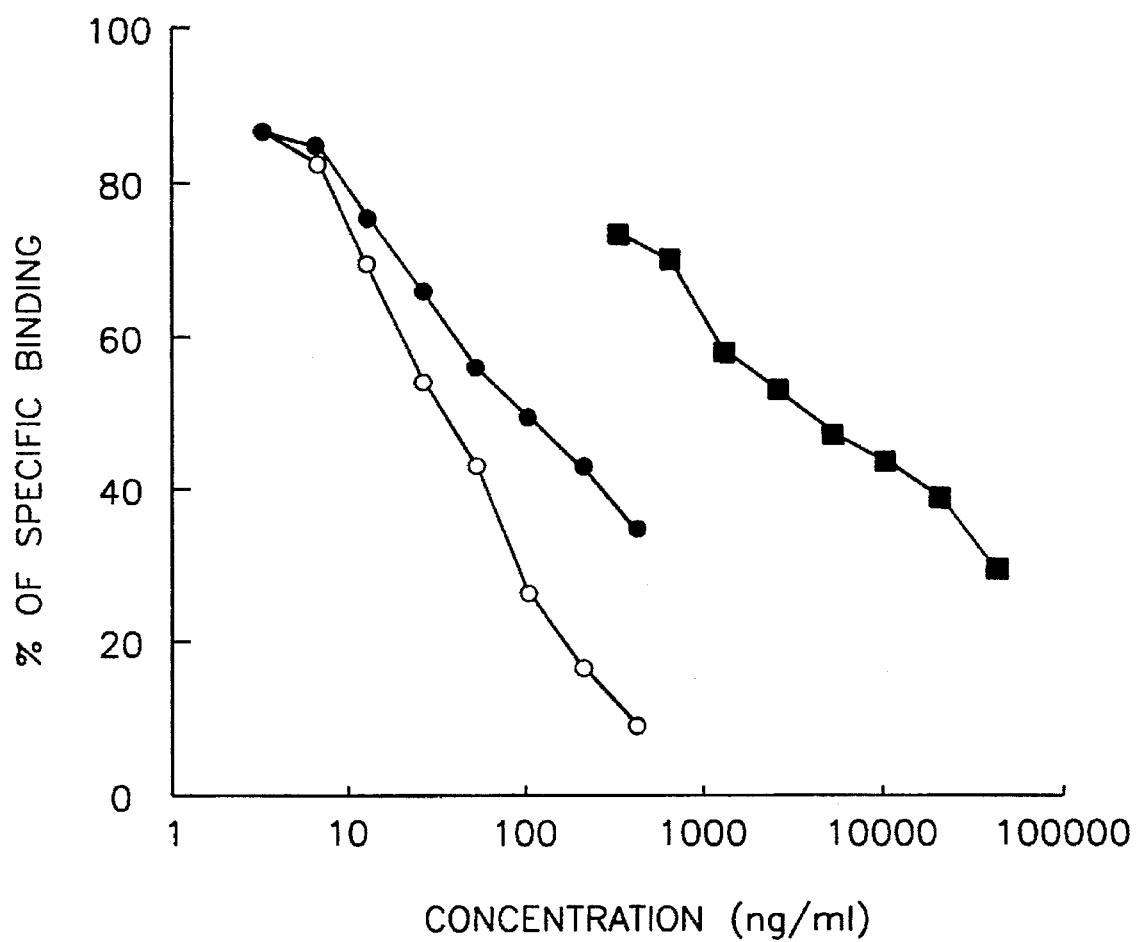
FIG. 7. Inhibition of [$^{125}$I]human IL-12 binding to human PHA-blasts by COS-expressed rp40 proteins. Varying concentrations of purified human IL-12 heterodimer (-●-), COS-expressed rp40 homodimer (-○-) or rp40 monomer (-■-) (determined by EIA using IL-12 as standard) were incubated with 1×10$^6$ PHA-blasts in the presence of 100 pM [$^{125}$I]human IL-12 for 1.5 h at room temperature. The data represent specific binding of [$^{125}$I]IL-12 and are expressed as percentage of the amount of [$^{125}$I]IL-12 bound to the cells in the presence of the indicated concentration of unlabeled IL-12 or rp40 proteins when compared with the total specific binding in the absence of unlabeled IL-12.

The Superdex 75 column fractions were tested for binding to KIT225 cells by FACS analysis. Binding activity correlated only with the 80 kDa p40-EIA positive protein (FIGS. 6A and 6B). The 80 and 40 kDa peak fractions were pooled separately, concentrated and examined in the competitive radioligand receptor binding assay (FIG. 7). The 80 kDa protein pool inhibited [$^{125}$I]human IL-12 binding to PHA-blasts with an $IC_{50}$ of 80 ng/ml, which is similar to the $IC_{50}$ of human IL-12 heterodimer (20 ng/ml). However, the slope of the competition curve by the 80 kDa homodimer differed from that of IL-12 heterodimer suggesting a different binding interaction with the receptor. The 40 kDa protein pool inhibited [$^{125}$I]human IL-12 binding with an $IC_{50}$ about one hundred times higher, which was probably due to a small amount of contamination with the p40 homodimer (FIG. 6B).

Figure 8:
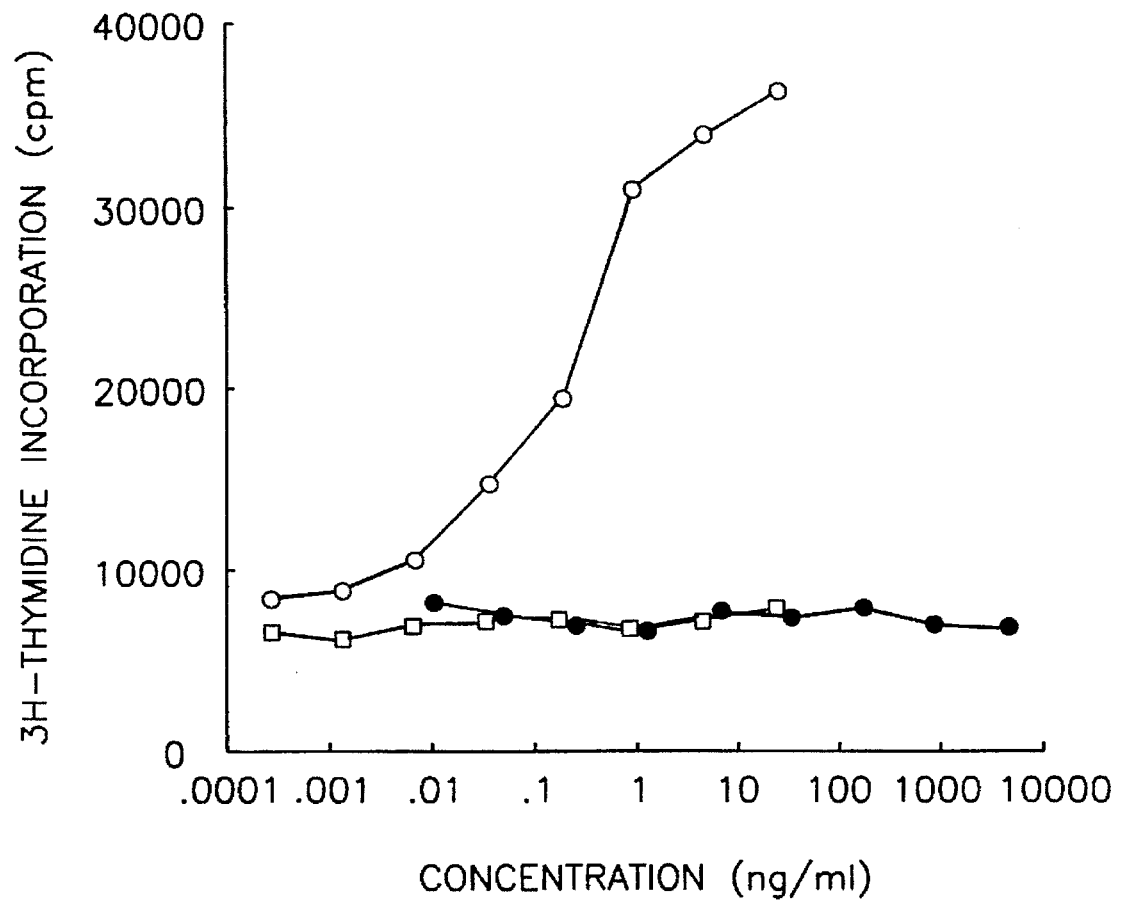
FIG. 8. COS-expressed human p40 homodimer induces little proliferation of human PHA-blasts. Serial dilutions of purified native human IL-12 (-○-), partially purified COS-expressed human rp40 homodimer (-●-), or PBS buffer (-[]-) were incubated with 2×10$^4$ PHA-blasts. Proliferation was measured in a 48 h assay as described in Materials and Methods. The concentration of rp40 was determined by a sandwich EIA using native human IL-12 as standard as described in Materials and Methods.
Figure 9:
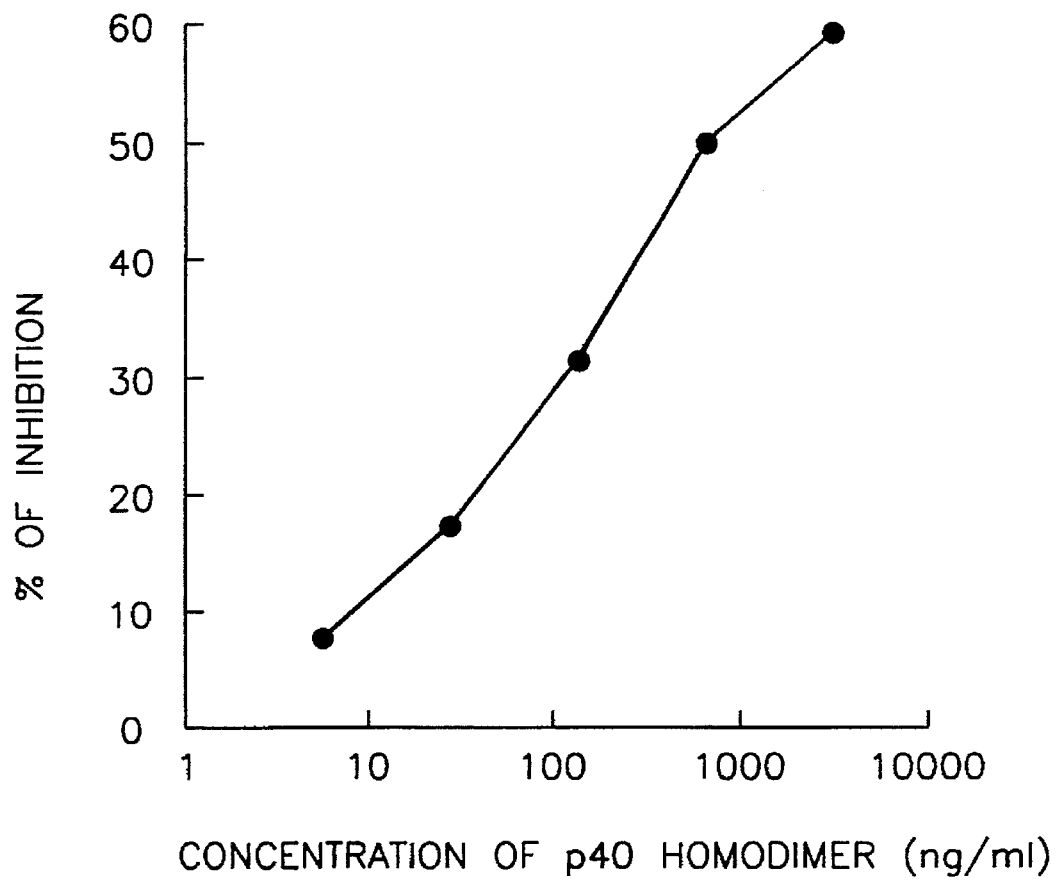
FIG. 9. Inhibition of IL-12 bioactivity by COS-expressed p40 homodimer. Varying concentrations of COS-expressed human rp40 homodimer were mixed with 0.1 ng/ml of native human IL-12 prior to incubation with 2×10$^4$ PHA-blasts. Neutralization of IL-12 bioactivity by COS-expressed p40 homodimer was measured in a 48 h proliferation assay as described in Materials and Methods. The data are expressed as the % inhibition of [$^3$H]thymidine incorporation in the presence of the indicated concentration of p40 homodimer as compared to [$^3$H]thymidine incorporation in the presence of an equivalent dilution of PBS buffer. The concentration of p40 was determined by a sandwich EIA using native human IL-12 as standard as described in Materials and Methods.

The abilities of the rp40 monomer and dimer to support PHA-blast proliferation were also examined (FIG. 8). No proliferative response was observed with either rp40 species even at concentrations 10,000 times higher than that of human IL-12 required to elicit a 50% maximum response. The rp40 dimer was tested for its ability to neutralize IL-12-dependent proliferation of PHA-blasts. The 80 kDa protein at varying concentrations was mixed with 0.1 ng/ml of human IL-12 and added to PHA-blasts. Dose-dependent inhibition of IL-12-induced proliferation of PHA-blasts was achieved with an $IC_{50}$ of µg/ml (FIG. 9).

IL-12 is unique among the lymphokines and cytokines in that it is a heterodimeric protein. Previous studies suggested that the p40 subunit is important for receptor binding (11, 12), and that the p35 subunit is primarily responsible for the species specificity observed in biological assays (13).

To further clarify the functional role of the individual subunits and localize the epitopes mediating biological and binding activities, we expressed the individual subunits alone or in combination with each other in COS cells and tested the expressed proteins in binding assays and bioassays and by Western blot analysis. The rp35 protein was inactive at concentrations as high as 100 ng/ml in the binding and bioassays; however, the rp40 protein reproducibly exhibited binding activity without bioactivity. Analysis of the conditioned media from cultures of COS cells transfected with only the p40 cDNA revealed that such media contained both monomeric p40 and an 80 kDa molecule reactive with anti-p40 antibodies. Partial purification of the rp40 by immunoaffinity chromatography and HPLC gel permeation chromatography revealed that the 80 kDa protein, but not the 40 kDa protein bound to the IL-12R.

Figure 5B:
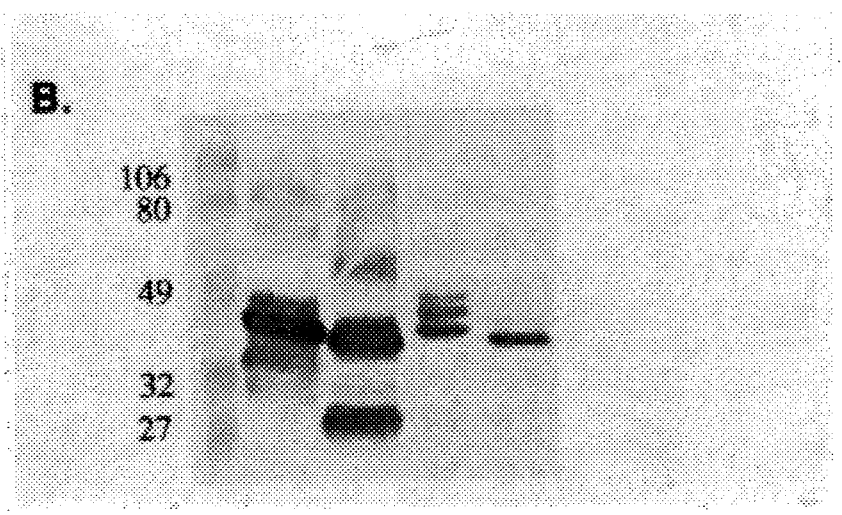

Unfortunately, no reagents were available to distinguish an 80 kDa p40 homodimer from the 75 kDa IL-12 heterodimer. The possibility that the 80 kDa protein was not a homodimer of p40 but a heterodimer consisting of one IL-12 p40 subunit and a second 35–40 kDa exogenous COS-derived protein was investigated. In particular, reports that many cell lines constitutively express IL-12 p35 mRNA (21) raised the possibility that the 80 kDa protein could be human IL-12 p40 associated with COS-derived IL-12 p35. Western blot analysis by using p35 specific antibody and deglycosylation experiments (FIGS. 5A and 5B) supported the notion that the 80 kDa protein could be reduced to a p40 monomer. The lack of bioactivity despite good binding activity further suggested that the second protein was not a COS-derived p35 IL-12 subunit (assuming no species restriction in the activity of monkey IL-12 on human cells). Also, expression of p40 in a baculovirus system yielded a biologically inactive 80 kDa form of p40 capable of binding to the receptor. It seems unlikely that insect cells produce an IL-12-like p35 protein. Most importantly, confirmation of the identity of the 80 kDa protein as p40 homodimer was provided by amino acid microsequencing of the protein demonstrating a single N-terminal sequence corresponding to the IL12 p40 subunit.

In competitive binding analysis, the p40 homodimer was found to bind to the IL-12R nearly as strongly as heterodimeric IL-12, suggesting that the key binding epitopes of IL-12 are localized in the p40 subunit. Though the $IC_{50}$ values for the heterodimer and the homodimer were similar, 20 and 80 ng/ml respectively, the slopes of the competition curves were different. This suggests a difference in the interaction of the two ligands with the receptor. It is most likely that the p40 binding epitopes are conformational and induced by association with a p35 or a second p40 subunit.

The IL-12 p40 subunit has been previously reported to be produced in excess of heterodimeric IL-12 both by activated B lymphoblastoid lines and by human PBMC stimulated to produce IL-12 (12, 23). It is possible that the p40 homodimer is formed in cells expressing p40/p35 heterodimers.

Figure 10A:
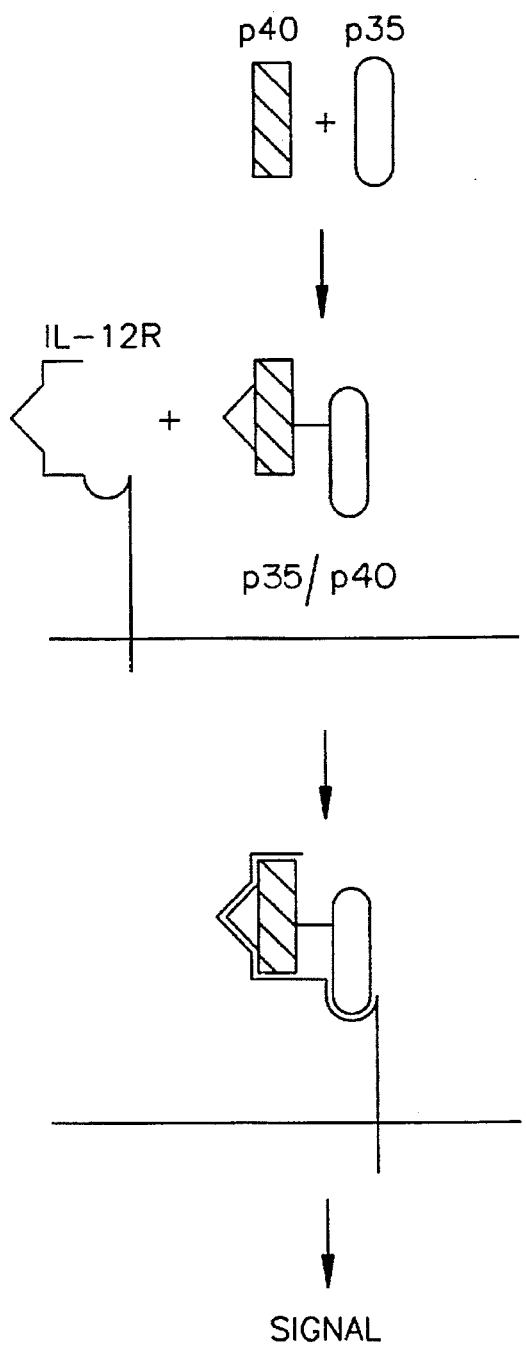
FIGS. 10A and 10B. Models of IL-12 p35/p40 heterodimer and p40/p40 homodimer binding to the IL-12 receptor and signal transduction. The IL-12 p40 subunit has to be associated with the p35 subunit or with another p40 molecule for proper conformation of the epitopes required for binding to the IL-12 receptor. However, only the heterodimer (FIG. 10A); not the homodimer (FIG. 10B) acts as a full agonist to induce signaling.
Figure 10B:
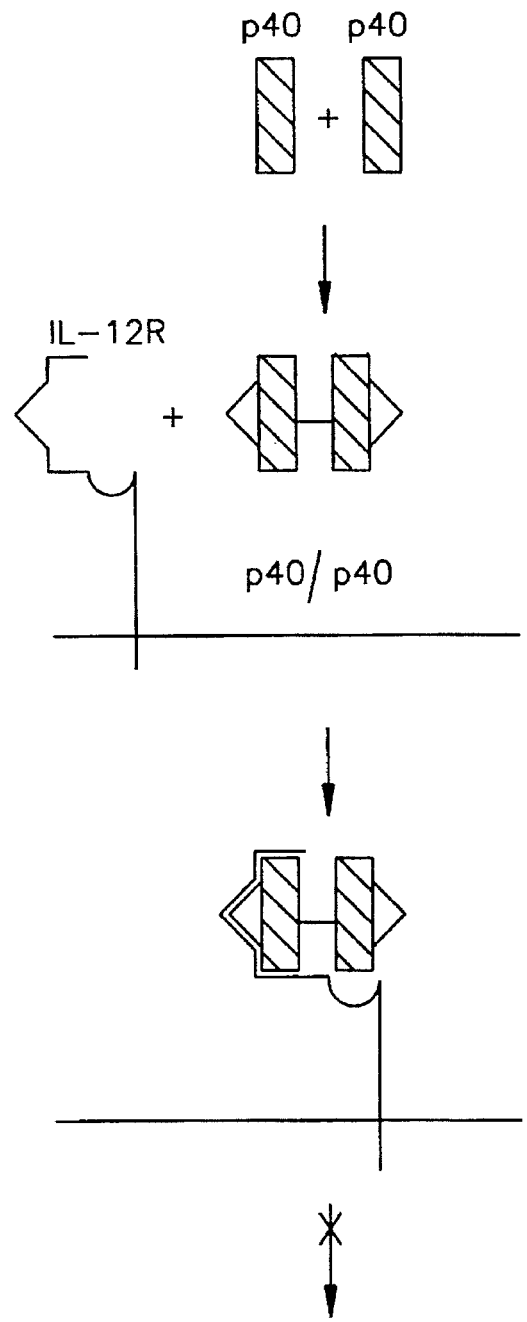

Based on our observations on the roles of the IL-12 subunits in binding and signaling, a model of IL-12 binding to its receptor is illustrated in FIGS. 10A and 10B. The p40 subunit contains the receptor binding epitopes that, however, are active only when p40 associates with a second protein, i.e. p35 or another molecule of p40. Both dimeric molecules bind to the IL-12R specifically, but only the dimer containing p35 acts as an agonist to mediate cellular transduction signals (FIG. 10A). In contrast, the p40/p40 dimer behaves as an antagonist to suppress IL-12 mediated responses (FIG. 10B). Gearing and Cosman (7) have suggested that IL-12 is analogous to a complex of cytokine and soluble receptor based on the homology between p40 and the interleukin 6 receptor (IL-6R). They also proposed that the cellular IL-12R probably is a gp 130-like signal-transducing protein. Our model of the interaction between p35, p40 and the IL-12R proposes that the IL-12/IL-12R system may function similarly to the IL-6R system. In the latter system, gp130 does not bind IL-6 (24), and neither IL-6 nor IL-6R alone stimulated proliferation of cells transfected with gp130 (25). Rather, the binding of IL-6 to IL-6R triggers the association of the receptor and gp130 (26), and in addition, complexes of IL-6 with soluble IL-6R can bind to gp130 to initiate signal transduction (26). Similarly, it appears that the association of IL-12 p40 with p35 results in an alteration in p40 that permits binding to IL-12R with subsequent initiation of p35-dependent, IL-12R-mediated signal transduction.

REFERENCES

1. Gately, M. K., B. B. Desai, A. G. Wolitzky, P. M. Quinn, C. M. Dwyer, F. J. Podlaski, P. C. Familletti, F. Sinigaglia, R. Chizzonite, U. Gubler, and A. S. Stern. 1991. Regulation of human lymphocyte proliferation by a heterodimeric cytokine, IL-12 (cytotoxic lymphocyte maturation factor). J. Immunol. 147:874.
2. Kobayashi, M., L. Fitz, M. Ryan, R. M. Hewick, S. C. Clark, S. Chan, R. Loudon, F. Sherman, B. Perussia, and G. Trinchieri. 1989. Identification and purification of natural killer cell stimulatory factor (NKSF), a cytokine with multiple biologic effects on human lymphocytes. J. Exp. Med. 170:827.
3. Chan, S. H., B. Perussia, J. W. Gupta, M. Kobayashi, M. Pospisil, H. A. Young, S. F. Wolf, D. Young, S. C. Clark, and G. Trinchieri. 1991. Induction of interferon gamma production by natural killer cell stimulatory factor: characterization of the responder cells and synergy with other inducers. J. Exp. Med. 173:869.
4. Stern, A. S., F. J. Podlaski, J. D. Hulmes, Y-C. Pan, P. M. Quinn, A. G. Wolitzky, P. C. Familletti, D. L. Stremlo, T. Truitt, R. Chizzonite, and M. K. Gately. 1990. Purification to homogeneity and partial characterization of cytotoxic lymphocyte maturation factor from human B-lymphoblastoid cells. Proc. Natl. Acad. Sci. USA 87:6808.
5. Wolf, S. F., P. A. Temple, M. Kobayashi, D. Young, M. Dicig, L. Lowe, R. Dzialo, L. Fitz, C. Ferenz, R. M. Hewick, K. Kelleher, S. H. Herrmann, S. C. Clark, L. Azzoni, S. H. Chan, G. Trinchieri, and B. Perussia. 1991. Cloning of cDNA for natural killer cell stimulatory factor, a heterodimeric cytokine with multiple biologic effects on T and natural killer cells. J. Immunol. 146:3074.
6. Gubler, U., A. O. Chua, D. S. Schoenhaut, C. M. Dwyer, W. McComas, R. Motyka, N. Nabavi, A. G. Wolitzky, P. M. Quinn, P. C. Familletti, and M. K. Gately. 1991. Coexpression of two distinct genes is required to generate secreted bioactive cytotoxic lymphocyte maturation factor. Proc. Natl. Acad. USA 88:4143.
7. Gearing, D. P. and D. Cosman. 1991. Homology of the p40 subunit of natural killer cell stimulatory factor (NKSF) with the extracellular domain of the interleukin-6 receptor. Cell 66:9.
8. Merberg, D. M., S. F. Wolf, and S. C. Clark. 1992. Sequence similarity between NKSF and the IL-6/G-CSF family. Immunology Today 13:77.
9. Chizzonite, R., T. Truitt, B. B. Desai, P. Nunes, F. J. Podlaski, A. S. Stern, and M. K. Gately. 1992. IL-12 receptor. I. Characterization of the receptor on phytohemagglutinin-activated human lymphoblasts. J. Immunol. 148:3117.
10. Desai, B. B., P. M. Quinn, A. G. Wolitzky, P. K. A. Mongini, R. Chizzonite, and M. K. Gately. 1992. IL-12 receptor. II. Distribution and regulation of receptor expression. J. Immunol. 148:3125.
11. Chizzonite, R., T. Truitt, F. J. Podlaski, A. G. Wolitzky, P. M. Quinn, P. Nunes, A. S. Stern, and M. K. Gately. 1990. IL-12: monoclonal antibodies specific for the 40-kDa subunit block receptor binding and biologic activity on activated human lymphoblasts. J. Immunol. 147:1548.
12. Podlaski, F. J., V. B. Nanduri, J. D. Hulmes, Y-C. E. Pan, W. Levin, W. Danho, R. Chizzonite, M. K. Gately, and A. S. Stern. (1992) Molecular characterization of interleukin 12. Arch. Biochem. Biophy. 294:230.
13. Schoenhaut, D. S., A. O. Chua, A. G. Wolitzky, P. M. Quinn, C. M. Dwyer, W. McComas, P. C. Familietti, M. K. Gately, and U. Gubler. 1992. Cloning and expression of murine IL-12. J. Immunol. 148:3433.
14. Hori, T., T. Uchiyama, M. Tsudo, H. Umadome, H. Ohno, S. Fukuhara, K. Kita, and H. Uchino. 1987. Establishment of an interleukin 2-dependent human T cell line from a patient with T cell chronic lymphocytic leukemia who is not infected with human T cell leukemia virus. Blood 70:1069.
15. Desai, B. B., T. Truitt, S. Honasoge, R. Warrier, R. Chizzonite, and M. Gately. 1993. Expression of functional IL-12R on a human IL-2-dependent T cell line. J. Immunol. 150:207A.
16. (a) Mizushima, S. and S. Nagata. 1990. pEF-BOS, a powerful mammalian expression vector. Nucleic Acids Research 18:5322. (b) Summers, M. D. and G. E. Smith. A manual of methods for baculovirus vectors and insect cell culture procedures. Texas A&M University, 1987.
17. Sambrook, J., E. F. Fritsch, and T. Maniatis. eds. 1989. Molecular Cloning: A laboratory manual. 2nd Edition, Cold Spring Harbor Press, Cold Spring Harbor, N.Y.
18. Guesdon, J-N., T. Ternynck, and S. A. Avrameas. 1979. The use of avidin-biotin interaction in immunoenzymatic techniques. J. Histochem. Cytochem. 27:1131.
19. Laemmli, U. K. 1970. Cleavage of structural proteins during assembly of the head of bacteriophage T4. Nature 227:680.
20. Hunkapiller, M. W., K. Granlund-Moyer, and N. W. Whitely. 1986. In Methods of Protein Microcharacterization (Shively, J. E., Ed), The Humana Press, Clifton, N.J., p.315.
21. Woff, S., D. Seiburth, B. Perussia, J. Yetz-Adalpe, A. D'Andrea, and G. Teinchieri. 1992. Cell sources of natural killer cell stimulatory factor (NKSF/IL-12) transcreipts and subunit expession. FASEB J. 6:A1335.
22. Hseih, C-S, S. E. Macatonia, C. S. Tripp, S. F. Wolf, A. O'Garra, and K. M. Murphy. 1993. Development of $T_H 1$ CD4$^+$ T cells through IL-12 produced by Listeria-induced macrophages. Science 260: 547–549.
23. D'Andrea, A., M. Rengaraju, N. M. Vailante, J. Chehimi, M. Kubin, M. Aste, S. H. Chan, M. Kobayashi, D. Young, E. Nickbarg, R. Chizzonite, S. F. Wolf, and G. Trinchieri. 1992. Production of natural killer cell stimulatory factor (interleukin 12 ) by peripheral blood mononuclear cells. J. Exp. Med. 176:1387.
24. Kishimoto, T., S. Akira, and T. Taga. 1992. Interleukin-6 and its receptor: a paradigm for cytokines. Science 258:593.
25. Hibi, M., M. Murakami, M. Saito, T. Hirano, T. Taga, and T. Kishimoto. 1990. Molecular cloning and expression of an IL-6 signal transducer, gp130. Cell 63:1149.
26. Taga, T., M. Hibi, Y. Hiram, K. Yamasaki, K. Yasukawa, T. Matsuda, T. Hirano, and T. Kishimoto. 1989.

Interleukin-6 triggers the association of its receptor with a possible signal transducer, gp130. Cell 58:573.

27. Manetti, R., P. Parronchi, M. G. Giudizi, M.-P. Piccinni, E. Maggi, G. Trinchieri, and S. Romagnani. 1993. Natural killer cell stimulatory factor (interleukin 12 [IL-12]) induces T helper type 1 (Th1)-specific immune responses and inhibits the development of IL-4-producing Th cells. J. Exp. Med. 177:1199.

28. D'Andrea, A., M. Rengaraju, N. M. Valiante, J. Chehimi, M. Kubin, M. Aste, S. H. Chan, M. Kobayashi, D. Young, E. Nickbarg, R. Chizzonite, S. F. Wolf, and G. Trinchieri. 1992. Production of natural killer cell stimulatory factor (interleukin-12) by peripheral blood mononuclear cells. J. Exp. Med. 176:1387.

29. Gately, M. K., A. G. Wolitzky, P. M. Quinn, and R. Chizzonite. 1992. Regulation of human cytolytic lymphocyte responses by interleukin-12. Cell. Immunol. 143:127.

30. Brod, S. A., D. Benjamin, and D. A. Hailer. 1991. Restricted T cell expression of IL-2/IFN-γ mRNA in human inflammatory disease. J. Immunol. 147:810.

31. Schlaak, J., E. Hermann, M. Ringhoffer, P. Probst, H. Gallati, K-H. M. zum Buschenfelde, and B. Fleischer. 1992. Predominance of $T_h1$-type T cells in synovial fluid of patients with Yersinia-induced reactive arthritis. Eur. J. Immunol. 22:2771.

32. Jacob, C. O., P. H. van der Meide, and H. O. McDevitt. 1987. In vivo treatment of (NZB×NZW)$F_1$ lupus-like nephritis with monoclonal antibody to γ interferon. J. Exp. Med. 166:798.

33. Campbell, I. L., T. W. H. Kay, L. Oxbrow, and L. C. Harrison. 1991. Essential role for interferon-γ and interleukin-6 in autoimmune insulin-dependent diabetes in NOD/Wehi mice. J. Clin. Invest. 87:739.

34. Doherty, G. M., J. R. Lange, H. N. Langstein, H. R. Alexander, C. M. Buresh, and J. A. Norton. 1992. Evidence for IFN-γ as a mediator of the lethality of endotoxin and tumor necrosis factor-α. J. Immunol 149: 1666.

We claim:

1. Isolated and purified p40 homodimer of Interleukin-12 having the amino acid sequence shown in SEQ ID NO:1.

2. The p40 homodimer of claim 1 having a molecular weight of about 80 kDa.

3. The p40 homodimer of claim 2 which binds to the receptor of Interleukin-12.

4. The p40 homodimer of claim 3 comprising two p40 subunits of Interleukin-12 which are linked together.

5. The p40 homodimer of claim 4 wherein the two p40 subunits are linked together by at least one disulfide bond.

6. The p40 homodimer of claim 5 wherein the p40 subunit is SEQ ID NO:1.

7. The p40 homodimer of claim 2 which blocks interleukin-12 biological activity.

8. A pharmaceutical composition which comprises an isolated and purified p40 homodimer of Interleukin-12, of claim 1 and a pharmaceutically acceptable carrier.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 306 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ile Trp Glu Leu Lys Lys Asp Val Tyr Val Val Glu Leu Asp Trp Tyr
 1               5                  10                      15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
                100                 105                 110

Asn Tyr Ser Gly Arg Phe Thr Cys Trp Trp Leu Thr Thr Ile Ser Thr
            115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
```

-continued

```
                        180                         185                         190

Val  His  Lys  Leu  Lys  Tyr  Glu  Asn  Tyr  Thr  Ser  Ser  Phe  Phe  Ile  Arg
                195                      200                      205

Asp  Ile  Ile  Lys  Pro  Asp  Pro  Pro  Lys  Asn  Leu  Gln  Leu  Lys  Pro  Leu
                210                      215                      220

Lys  Asn  Ser  Arg  Gln  Val  Glu  Val  Ser  Trp  Glu  Tyr  Pro  Asp  Thr  Trp
      225                      230                      235                           240

Ser  Thr  Pro  His  Ser  Tyr  Phe  Ser  Leu  Thr  Phe  Cys  Val  Gln  Val  Gln
                          245                      250                           255

Gly  Lys  Ser  Lys  Arg  Glu  Lys  Lys  Asp  Arg  Val  Phe  Thr  Asp  Lys  Thr
                     260                      265                      270

Ser  Ala  Thr  Val  Ile  Cys  Arg  Lys  Asn  Ala  Ser  Ile  Ser  Val  Arg  Ala
                     275                      280                      285

Gln  Asp  Arg  Tyr  Tyr  Ser  Ser  Ser  Trp  Ser  Glu  Trp  Ala  Ser  Val  Pro
                290                      295                      300

Cys  Ser
      305
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
      Ile  Trp  Glu  Leu  Lys  Lys  Asp  Val  Tyr  Val
      1                 5                            10
```